United States Patent [19]

Ponsi et al.

[11] Patent Number: 5,387,735
[45] Date of Patent: Feb. 7, 1995

[54] SHARPS DISPOSAL CONTAINER AND SYSTEM

[75] Inventors: Lawrence G. Ponsi, Wheeling; Barbara T. Skiba, Chicago; David McDonough, Crystal Lake, all of Ill.

[73] Assignee: Sage Products, Inc., Crystal Lake, Ill.

[21] Appl. No.: 44,590

[22] Filed: Apr. 8, 1993

[51] Int. Cl.⁶ .................... A62D 3/00; B65D 83/10
[52] U.S. Cl. ................... 588/249; 206/366; 220/908; 405/128
[58] Field of Search ............ 405/128; 588/249; 206/366; 220/908

[56] References Cited

U.S. PATENT DOCUMENTS

| | | | |
|---|---|---|---|
| 4,890,733 | 1/1990 | Anderson | 206/366 X |
| 4,903,832 | 2/1990 | Stewart | 206/366 |
| 5,076,429 | 12/1991 | Patrick et al. | 220/908 X |
| 5,178,322 | 1/1993 | Shillington | 206/366 X |

Primary Examiner—Dennis L. Taylor
Attorney, Agent, or Firm—Lee, Mann, Smith, McWilliams, Sweeney & Ohlson

[57] ABSTRACT

A disposal container and a disposal system employing the disposal container. The container comprises a hollow container body having an opening at the top to permit access to the interior of the container body and having a barrier disposed adjacent the opening for restricting access to the interior of the container body. The barrier at least in part comprises a first cowl extending over the opening and a complementary second cowl extending beneath the opening, with the second cowl being offset relative to the first. The container includes a retention for preventing items from being dispensed through the opening from the interior of the container body when the container body is upright. The outer enclosure is shaped to accommodate the inner container, and includes a hood conforming to the first cowl.

19 Claims, 6 Drawing Sheets

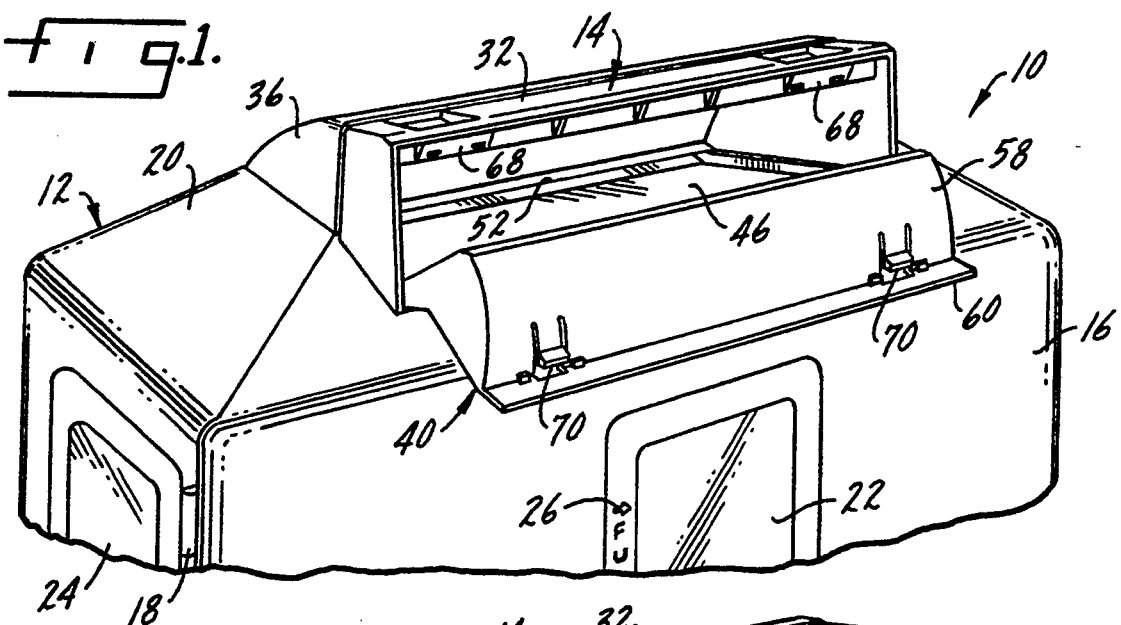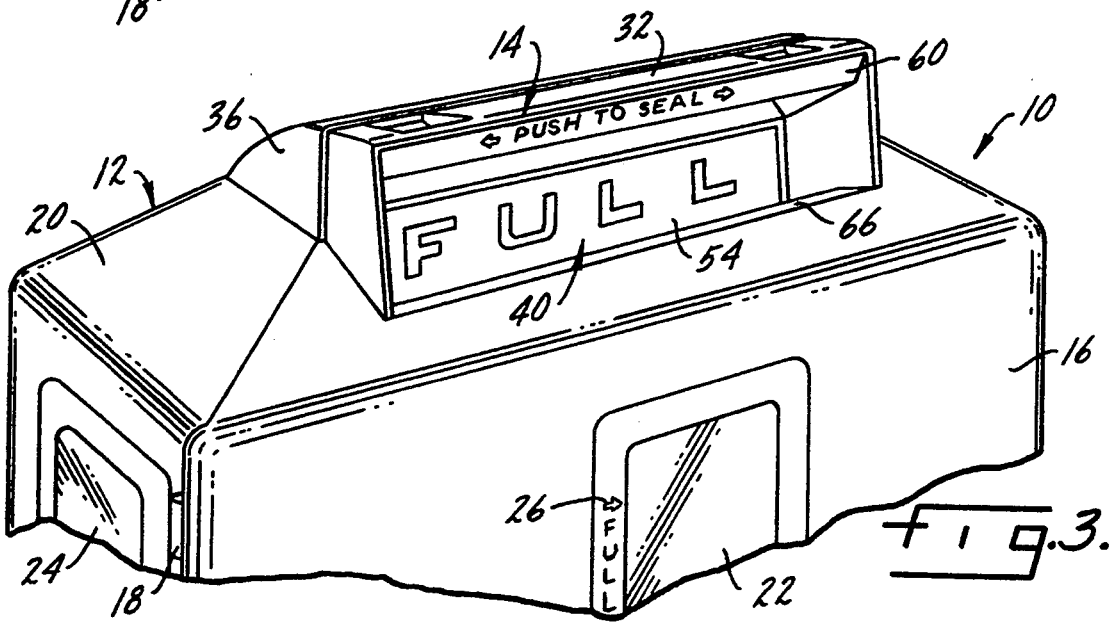

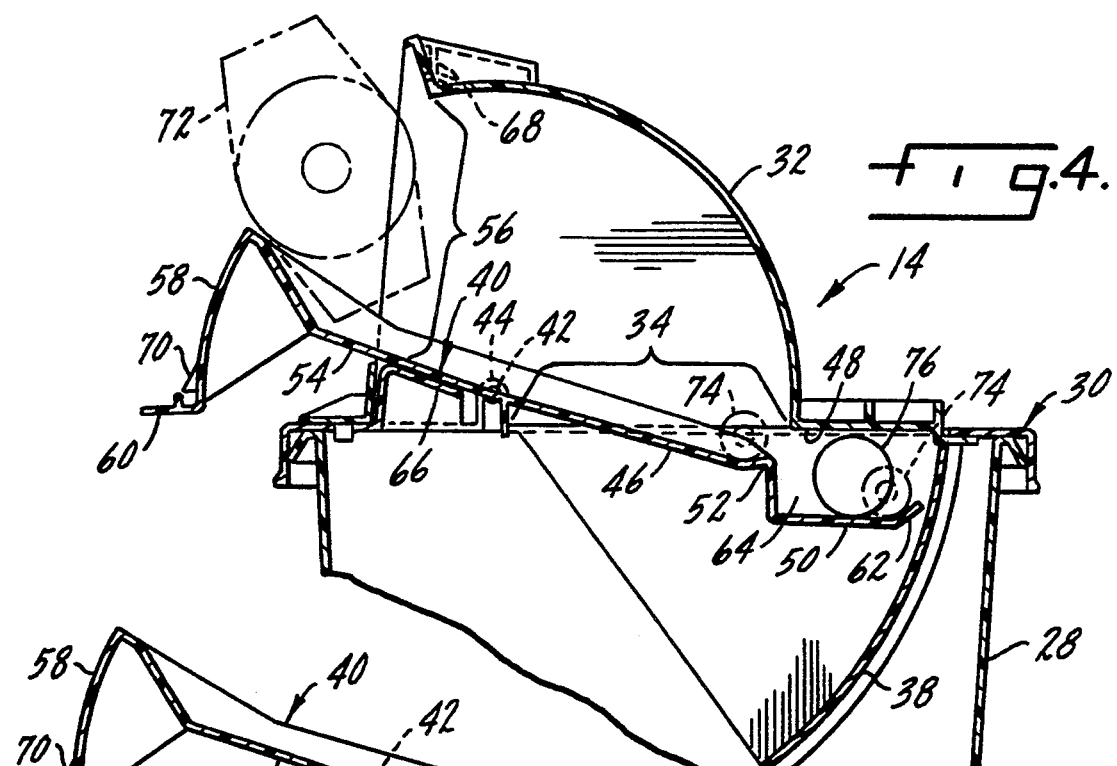
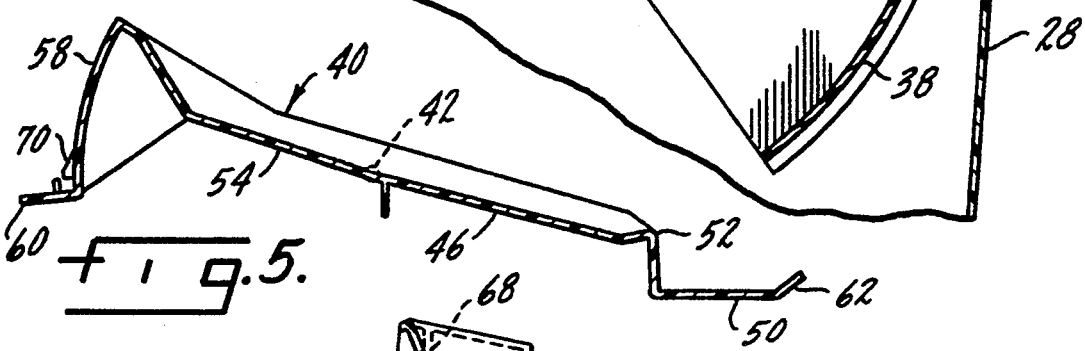
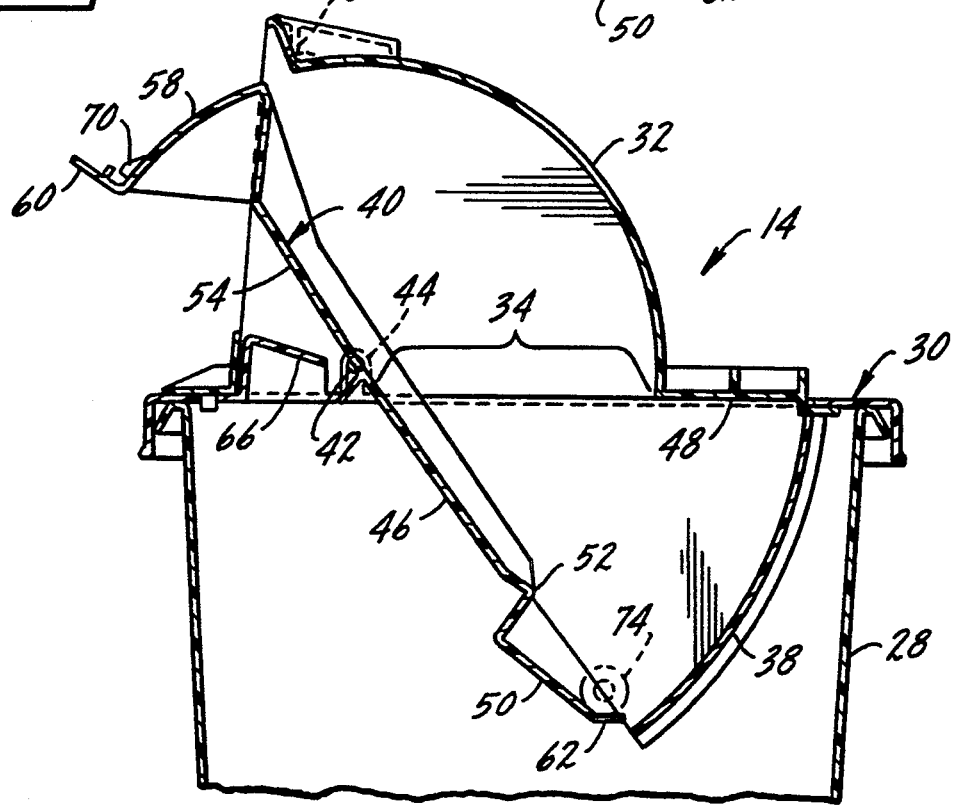

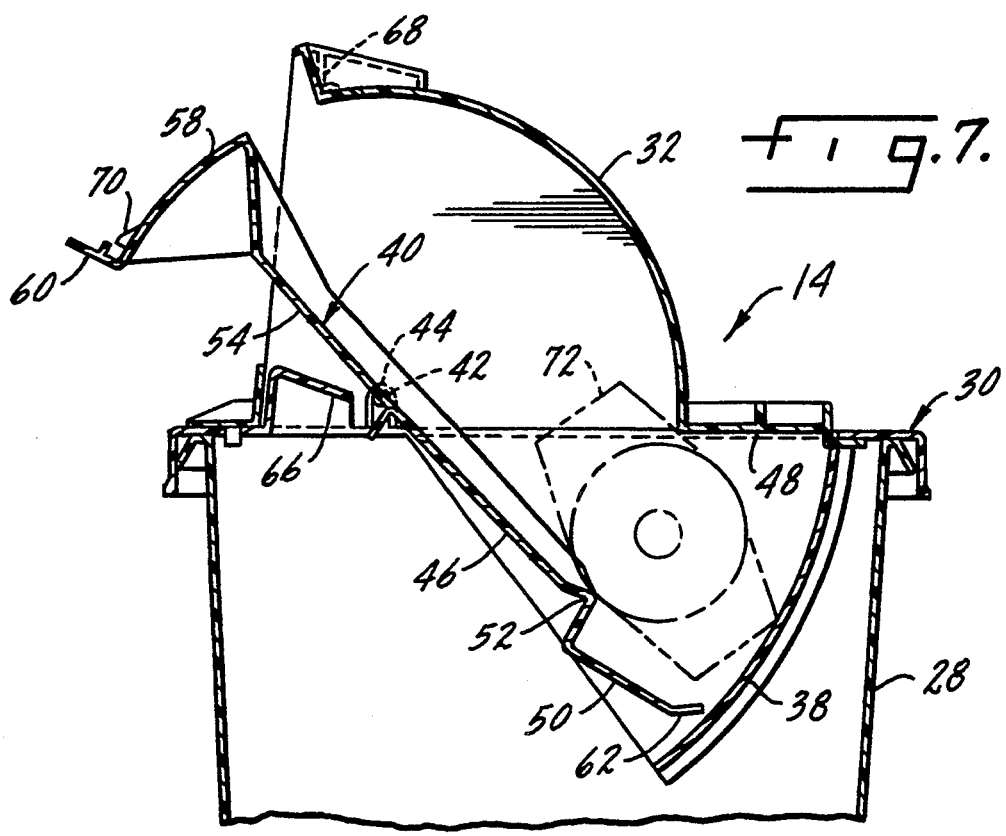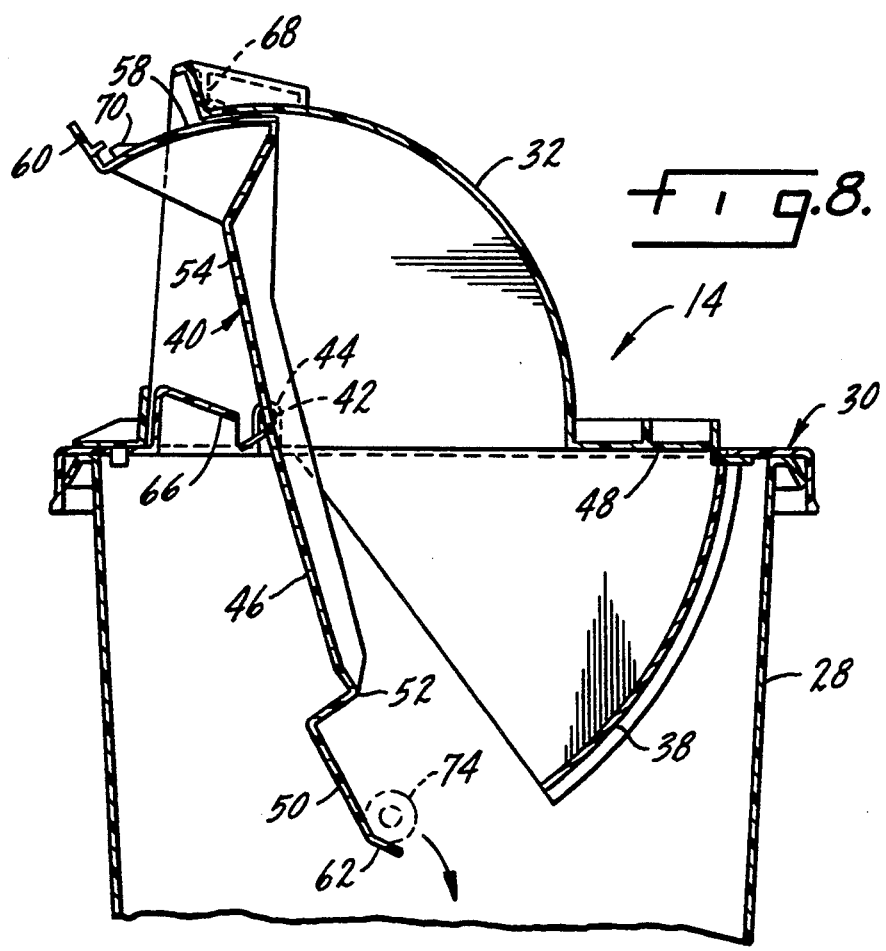

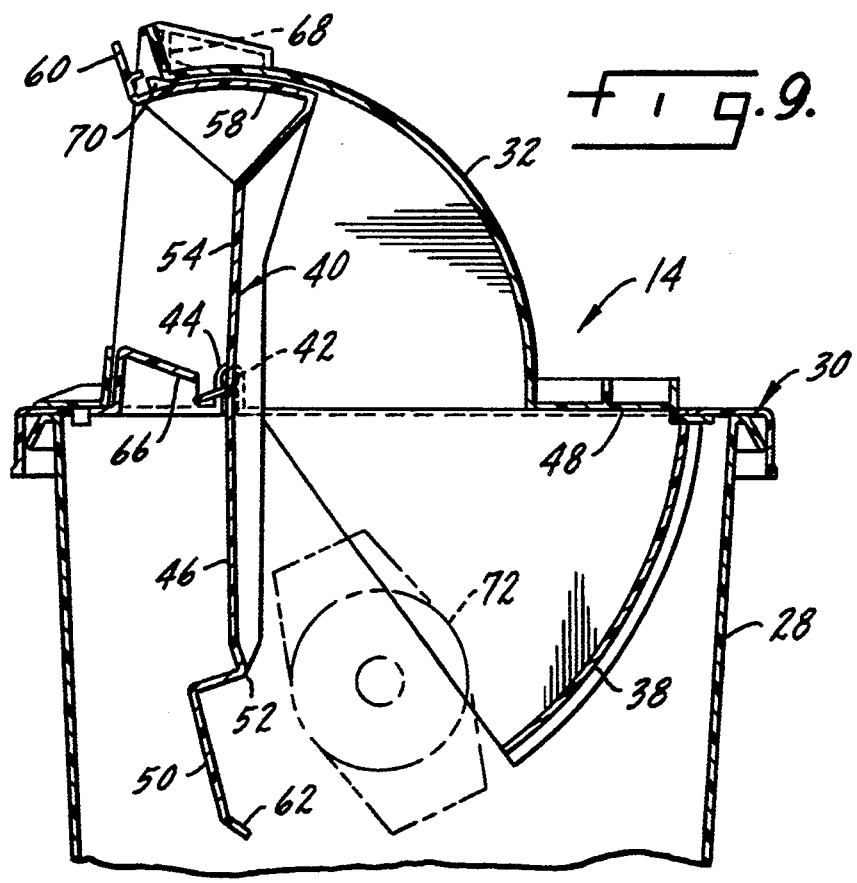
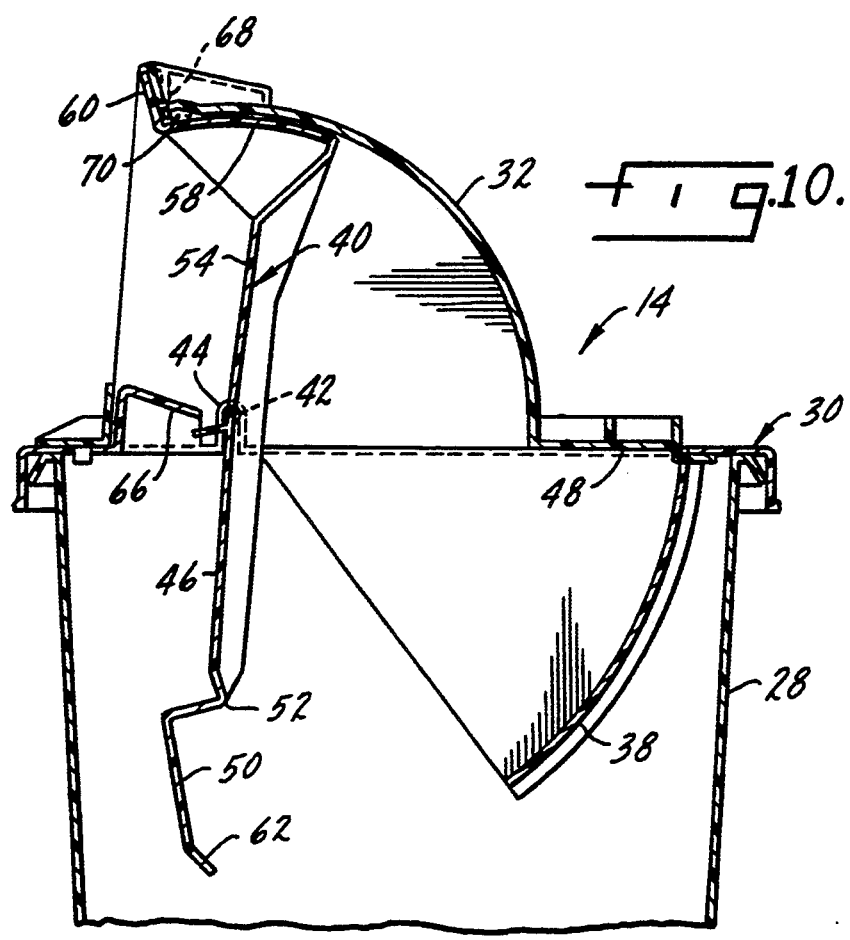

SHARPS DISPOSAL CONTAINER AND SYSTEM

BACKGROUND OF THE INVENTION

This invention relates to disposal of contaminated items, and in particular to a disposal system for use in a hospital or similar environment where contaminated items must be collected and disposed of without creating a hazard for patients or hospital personnel.

In hospitals, clinics and similar medical institutions, contamination continues to be of utmost concern. With the prevention of the spread of communicable diseases being a major priority, disposable, single use patient-use care products have become quite prevalent. Those items, once used, are contaminated and can readily transmit disease. They include items such as hypodermic needles and other sharps, and are required to be disposed of at their point of usage under current guidelines of the United States Centers for Disease Control. In U.S. Pat. Re. No. 33,413, the disclosure of which is incorporated herein by reference, and U.S. Pat. No. 4,779,728, the disclosure of which is incorporated herein by reference, sharps disposal systems are described. The present invention is an improvement over those systems.

SUMMARY OF THE INVENTION

The invention provides a hollow, upstanding container body having an opening at the top of the container body for permitting access to the interior of the container body. A barrier is disposed proximate the opening for restricting access to the interior of the container body, at least a portion of the barrier comprising a first constriction extending over the opening and a second constriction extending beneath the opening. Retention means is provided for preventing items from being dispensed through the opening from the interior of the container body when the container body is upright.

In accordance with the preferred form of the invention, the disposal container includes a closure disposed adjacent to the opening. The closure preferably is pivotal, and the retention means comprises the combination of two features of the invention, shaping of a portion of the closure to extend across the opening and positioning of the second constriction in an offset fashion relative to the opening. The second constriction comprises a cowl extending into the interior of the container body, the cowl being located at one longitudinal side of the opening and the closure being pivotally disposed at an opposite longitudinal side of the opening. The closure pivots about a longitudinal pivot axis, and the cowl is shaped to be radially equidistant from the pivot axis at all locations.

The offsetting of the second constriction from the first provides a longitudinal obstruction extending between the opening and the second constriction. The closure is provided with a terminal end which is shaped to engage that obstruction. Also, the closure is provided with a heel adjacent to the terminal end, with the heel being shaped to engage the first constriction when the terminal end engages the longitudinal obstruction.

The closure also includes a portion shaped to engage and close the first constriction. An activation flap extends from and is coextensive with a terminal edge of that portion to permit pivoting of the closure. The closure also includes means biasing the closure such that it normally remains in an opened orientation. Preferably, the biasing means is a counterweight, the flap including the counterweight as an integral portion thereof.

In accordance with the preferred forms of the invention, the first constriction includes means for locking the closure to prevent access to the interior of the container body when locked. To this end, within the cowl of the first constriction is included at least one catch. The catch includes a stop which engages the closure when the closure is pivoted in one direction past the stop into the interior of the cowl. At that orientation, the stop prevents pivoting of the closure in an opposite direction to reopen the container.

The disposal system according to the invention may include the disposal container as an inner container within a hollow, outer enclosure. The outer enclosure is shaped to accommodate and conform at least in part to the inner container. Preferably, the outer enclosure includes a hood, with the hood being shaped to conform to the first constriction and being located in registration with the constriction when the container is located within the outer enclosure.

BRIEF DESCRIPTION OF THE DRAWINGS

The invention is described in greater detail in the following description of examples embodying the best mode of the invention, taken in conjunction with the drawings, in which:

FIG. 1 is a perspective view of a top portion of a disposal system according to the invention, with one form of disposal container located within a hollow enclosure, and with the closure of the disposal container being fully opened, FIG. 2 is a view similar to FIG. 1, but with the closure of the disposal container being partially closed, FIG. 3 is a view similar to FIGS. 2 and 1, but with the closure for the disposal container being fully closed, FIG. 4 is an enlarged partial cross sectional view through only the disposal container illustrated in FIG. 1, showing the closure being in the opened orientation and illustrating disposable sharps at various positions of disposal, FIG. 5 is a cross sectional view of the closure of FIG. 4, FIG. 6 is a view similar to FIG. 4, but with the closure being partially closed just prior to dropping a small disposed item within the container body, FIG. 7 is a view similar to FIG. 6, but showing disposal of a larger sharps, FIG. 8 is a view similar to FIG. 6, but showing the closure fully rotated so that the disposed item drops within the container body, FIG. 9 is a view similar to FIG. 7, but showing the closure fully rotated so that the large disposed sharps drops within the container body, FIG. 10 is a view similar to FIGS. 8 and 9, but with the closure fully rotated to a locked orientation.

DESCRIPTION OF EXAMPLES EMBODYING THE BEST MODE OF THE INVENTION

Figure 11:
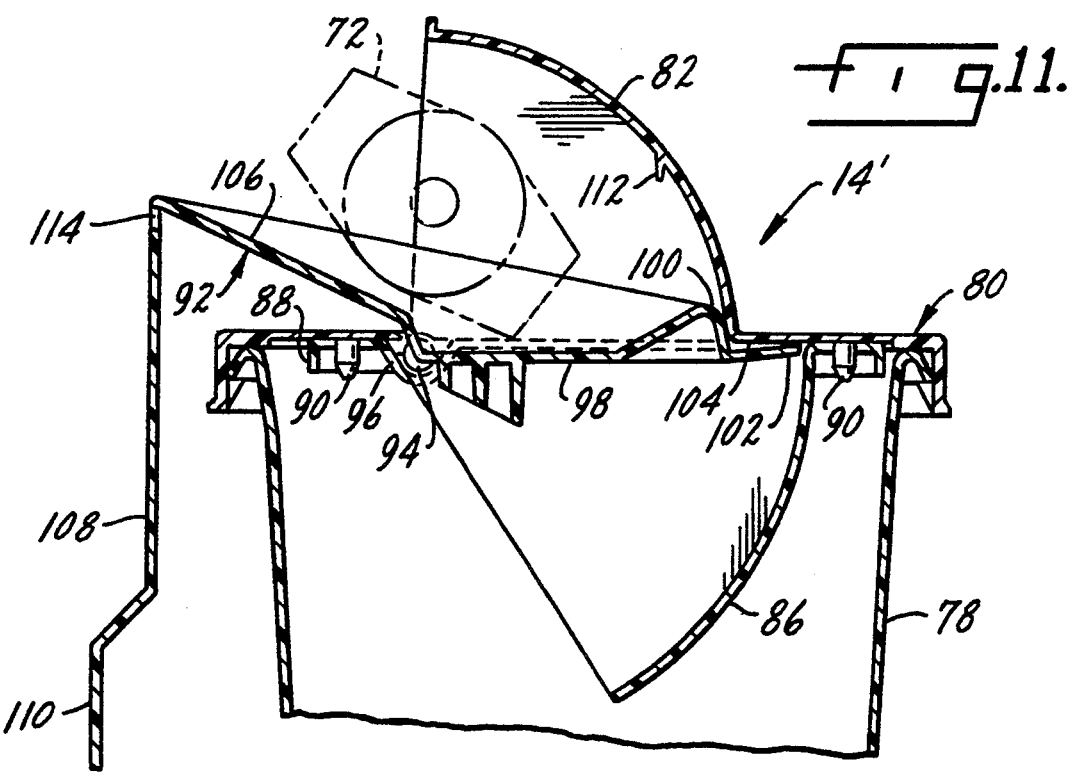
FIG. 11 is a cross sectional view similar to FIG. 4, but of a second embodiment of the invention, and showing a large sharp in phantom as it is placed upon the closure for disposal.

A sharps disposal system according to the invention is designated generally at 10 in the drawing figures. Primary components of the system 10 are a hollow, outer enclosure 12 and an inner, disposal container 14 shaped to be located within the outer enclosure 12. The outer enclosure 12 is illustrated only in FIGS. 1–3, it being evident that the inner disposal containers 14 illustrated in the ensuing drawing figures, although not illustrated in combination with an outer enclosure 12, are intended to fit within an outer enclosure in many, but not necessarily all, instances of use.

The outer enclosure 12 includes an access door 16 secured by one or more hinges 18 to a main body 20 of the enclosure 12. Both the outer enclosure 12 and the inner container 14 are preferably made of various plastic materials, and if the inner container 14 is made of a translucent or transparent material, the door 16 can include a window 22 and the main body 20 can include one or more windows 24 for viewing the contents of the disposal container 14. One or more of the windows 22 and 24 can include an indication 26 to show when the inner container 14 is sufficiently fully of sharps that it should be removed and emptied or replaced.

Other features of the outer enclosure 12 may be included as desired. For example, preferably the door 16 includes some means for it to be locked to avoid tampering with the contents of the outer enclosure 12. Also, other adjunct features can be incorporated into the outer enclosure 12, such as a glove dispenser as disclosed in U.S. Pat. No. 4,863,057. Any number of other features might be incorporated in the outer enclosure as desired.

The inner disposal container 14 is composed of a receptacle 28 and a top or cover 30 which is preferably snap-fitted onto the receptacle 28 in a conventional fashion. Other means of attachment can be employed as desired. The receptacle 28 and the cover 30 are preferably formed of injection-molded plastic, and if the windows 22 and 24 are employed in the outer enclosure 12, it is preferred that at least the receptacle 28 be of translucent or transparent material so that the contents thereof can be viewed through the windows 22 and 24. Also, while the inner disposal container 14 is shown being formed of two basic components, the receptacle 28 and the cover 30, it should be apparent that, depending on manufacturing capabilities and the desire of the user, the receptacle 28 might be formed of more than one piece, or the receptacle 28 and the cover 30 can be formed in an integral fashion.

The cover 30 includes several features. It has an integral cowl 32 extending over an opening 34 through the cover 30. The opening is provided for permitting access to the interior of the inner container 14, and the cowl 32 extends for the length and width of the opening 34. Also, as best shown in FIGS. 1–3, the cowl 32 is generally coextensive with a hood 36 formed in the outer enclosure 12. The cowl 32 forms a first constriction extending over the opening 34.

The cover 30 is provided with a second cowl 38 extending beneath the cover 30 as shown. The cowl 38 forms a second constriction extending beneath the opening 34, and the cowls 32 and 38 form at least part of a barrier for restricting access by a user to the interior of the inner container 14.

A pivotal closure 40 is mounted in the cover 30 at one side of the opening 34. The closure 40 extends for the length of the opening 34, and includes pivot pins 42 at opposite ends thereof, each of which extends into a pivot bracket 44 formed in the cover 30. Other means of pivoting can be employed, as well.

The closure 40 has an inner portion 46 shaped to extend across the opening 34. The lower cowl 38 is offset from the upper cowl 32, forming a longitudinal obstruction 48 extending between the opening 34 and the cowl 38. The closure 40 also includes a terminal end 50 extending from the inner portion 46 and shaped to engage the obstruction 48. A heel 52 is also formed in the closure 40 at the juncture of the inner portion 46 and the terminal end 50.

Opposite the pivot pins 42, the closure 40 includes an outer portion 54 forming a platform for receipt of sharps and also extending sufficiently to close a mouth 56 of the cowl 32, as best shown in FIGS. 8–10.

The outer portion 54 terminates at a flap 58 having a curvature sufficient to mate with the curvature of the cowl 32. The flap 58 also has a grip 60 to allow the user to readily manipulate the closure 40 when using the disposal container 14.

The closure 40 pivots about a pivot axis extending through the opposite pivot pins 42. The terminal end 50 extends to an up-turned tip 62 proximate the cowl 38. The curvature of the cowl 38 is such that the tip 62 is always in close proximity to the cowl 38, and therefore preferably the cowl 38 is, at all points, radially equidistant from the pivot axis extending between the pins 42.

The terminal end 50 is downwardly offset from the inner portion 46. The obstruction 48 is formed from an outward offsetting of the cowl 38 from the opening 34. The obstruction 48 and terminal end 50 form a retention pocket or means 64 for preventing sharps from being dispensed through the opening 34 from the interior of the container 14 when the container is upright. The pocket 64 occurs because the closure 40 butts against a shelf 66 formed in the cover 30. If the shelf 66 were not included (as is the case in the second embodiment of FIGS. 11–14), the terminal end 50 would essential mate with the obstruction 48, eliminating any retention pocket per se, but still providing the retention means, as explained further below.

Means is also provided for essentially permanently locking the closure 40 to prevent access to the interior of the container 14. At least one catch 68 is provided in the cowl 32, in alignment with an engaging member 70 formed in the flap 58. When the closure 40 is fully rotated to the closed positioned shown in FIG. 10, the engaging member 70 engages behind the catch 68, preventing rotation of the closure 40 in the opposite direction.

In use, as shown in FIGS. 4–8, a used sharp 72, 74 or 76 is placed on the outer portion 54 of the closure 40 when opened, typically one at a time. The user then pivots the closure 40 upwardly in relation to the grip 60, causing the sharp to first fall into the container 14 and rest against the inner cowl 38. Further rotating of the closure then causes the used sharp to drop into the interior of the container 14.

During the disposal process, once a sharp 70–76 has fallen sufficiently into the container 14 that it abuts the cowl 38, the closure 40 cannot be reopened to inadvertently eject the sharp from the interior of the container 14. This is due to the downward offset of the terminal end 50 in combination with the lateral offset of the cowl 38. Once a sharp is in the position of the pocket 64, it is captured within the container 14, and cannot be ejected back through the opening 34. Rather, the closure 40 must continue to be pivoted until the sharp drops within the interior of the container 14.

This phenomenon is first demonstrated with the relatively large sharp 72. As shown in FIG. 4, when the sharp 72 is to be disposed, it is placed on the closure 40 and, although not illustrated, due to the inclination of the closure 40, normally slides or rolls until it abuts the cowl 32 above the inner portion 46. Then, as shown in FIG. 7, the closure 40 is pivoted, causing the sharp 72 to fall until it abuts the cowl 38. At this position, the closure 40 cannot be pivoted in the opposite direction, since the sharp 72 is lodged between the obstruction 48 and either the terminal end 50 or the heel 52 (or both). The user must further rotate the closure 40, as shown in FIG. 9, until the sharp 72 drops within the interior of the container 14.

Similar results occur with smaller sharps 74 and 76. As shown in FIG. 4, once a sharp 74 or 76 is within the pocket 64, it cannot be ejected since it is captured between the terminal end 50 and the obstruction 48. Rather, in order to release the sharp 74 or 76, the closure must be pivoted as shown in FIGS. 6 and 8 until the sharp drops within the interior of the container 14.

Once the receptacle 28 has been filled or if it is desired to remove a partially filled container 14 from the outer enclosure 12, as shown in FIG. 10, the closure 40 is pivoted fully upright until the engaging member 70 engages behind the catch 68. The closure 40 is then essentially locked in place, and the container 14 can be disposed of appropriately.

A second embodiment of the inner disposal container is shown in FIGS. 11-14. While the container 14' is generally similar to, and shares common basic features of, the container 14, some differences exist, as well.

The container 14' is composed of two basic portions, a receptacle 78 and a cover 80. The receptacle 78 can be identical to the receptacle 28 of the first embodiment of the invention. The receptacle 78 and the cover 80 may be joined in any fashion, as explained in connection with the first embodiment of the invention.

The cover 80 includes an upper cowl 82 extending above, and coextensive with, an opening 84 to the interior of the receptacle 78. A second, lower cowl 86 extends beneath the cover 80 and opening 84, in precisely the same manner as the first embodiment of the invention. The cowl 86 may be an integral extension of the cover 80, or, as illustrated, may include a peripheral flange 88 which is attached to the underside of the cover 80, such as on a series of pins 90. The cowl 86 can be appropriately affixed to the underside of the cover 88 in any conventional manner as desired.

A closure 92 is pivotally mounted at one side of the opening 84. The closure 92 includes opposite pivot pins 94 engaged in opposite sockets 96 formed in the cover 80. Therefore, the closure 92 pivots about a pivot axis extending through the opposite pivot pins 94.

The closure 92 includes an inner portion 98 shaped to close the opening 84. The inner portion 98 includes a heel 100 which, as shown in FIG. 11, is shaped to engage the inner surface of the cowl 82. A terminal end 102 extends from the inner portion 98, coextensive with an obstruction 104 formed by the offset of the cowl 86 from the opening 84. The heel 100, terminal end 102 and obstruction 104 form a retention for preventing sharps from being dispensed through the opening 84 from the interior of the receptacle 78 in use, as explained in a bit greater detail below.

The closure 92 also includes an outer portion 106, with an activation flap 108 extending from an outer terminal edge of the outer portion 106. The flap 108 extends to a grip 110 at a distal edge thereof.

The closure 92 is freely pivotal about its pivot pins 94. Preferably, the flap 108 and grip 110 are sized such that their combined mass biases the closure 92 in the opened orientation shown in FIG. 11. The flap 108 and grip 110 counterweight the oppositely extending inner portion 98 and terminal end 102. The amount of material in the flap 108 and grip 110 can be chosen judiciously so that the closure 92 allows automatic ejection of a sharp 72 when placed on the inner portion 98, as explained in greater detail.

For permanent locking of the closure 92 when the receptacle 78 is filled with waste or when it is desired to be discarded, the cowl 82 includes at least one catch 112 extending downwardly and in alignment with a series of apertures 114 formed in the flap 108. The catch 112 forms a stop which engages the aperture 114 when the flap 108 is pushed to engage the catch 112 in an aperture 114.

Figure 12:
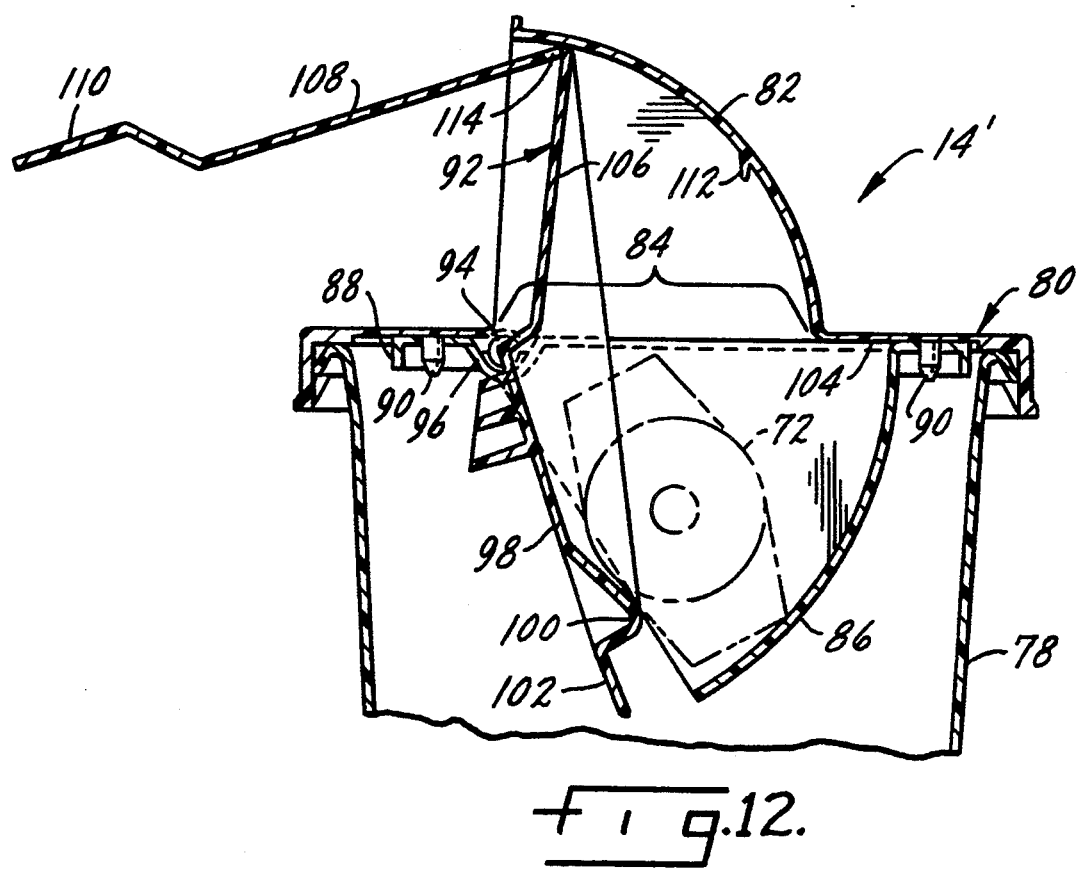
FIG. 12 is a view similar to FIG. 11, but with the closure partially closed, initially dropping the sharp to a second orientation within the container body.
Figure 13:
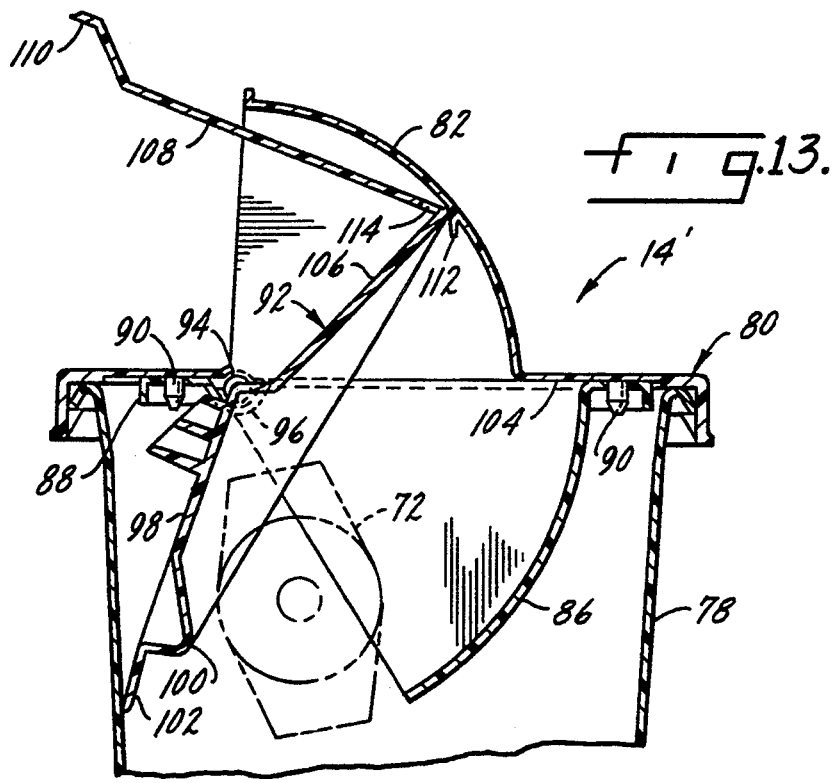
FIG. 13 is a view similar to FIG. 12, but with the closure fully closed (but not locked), and showing the sharp dropping within the container body.
Figure 14:
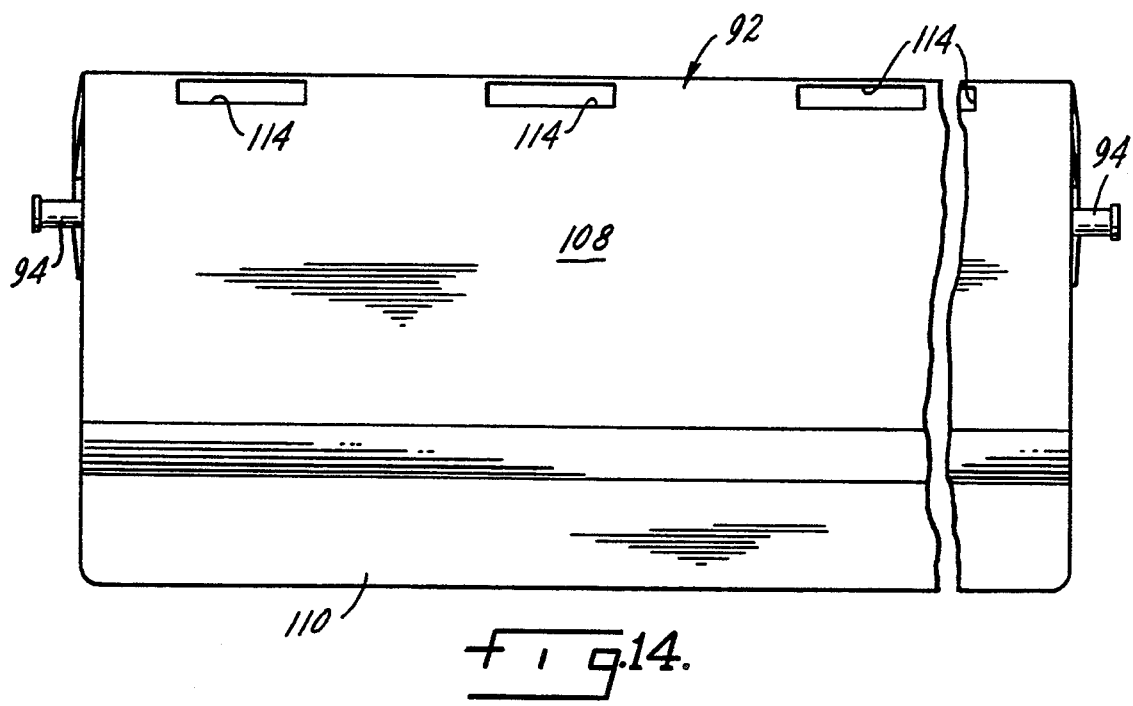
FIG. 14 is a front elevational view of the closure of FIGS. 11–13.

In use, a sharp 72 to be discarded within the container 14' is placed on the inner portion 98. If sufficiently massive, the weight of the sharp 72 causes the closure 92 to pivot as shown in the sequence of FIGS. 11-13, dropping the sharp 72 within the receptacle 78. If the sharp 72 does not have sufficient weight to overbalance the counterbalancing of the weight of the flap 108 and grip 110, the user can simply lift the flap 108 at the grip 110, causing the sharp 72 to fall within the receptacle 78 in exactly the same fashion as explained in connection with the first embodiment of FIGS. 1-10. Also, due to the offset forming the obstruction 104, in combination with the heel 100 and terminal end 102, once a sharp 72 engages the lower cowl 86, it is captured, and cannot be returned through the opening 84 if the rotational direction of the closure 92 is reversed.

Once the receptacle 78 is filled or desired to be discarded, the closure 92 is locked by pushing the flap 108 until the catches 112 engage the apertures 114. The closure 92 is then locked in place.

In this form of the invention, the user is prevented from reaching into the interior of the receptacle 78 due to the cooperation of the two cowls 82 and 86. In addition, as best shown in FIG. 12, the closure 92 cooperates with the cowls 82 and 86 to serve as a further barrier to the interior of the receptacle 78. Only when the outer portion 106 is engaged beneath the cowl 82 does the terminal end 102 extend past the cowl 86. Therefore, the user is doubly protected from any means of inadvertently extending fingers within the receptacle 78.

Various changes can be made to the invention without departing from the spirit thereof or scope of the following claims.

What is claimed is:

1. A disposal container comprising
   a. a hollow, upstanding container body,
   b. an opening at the top of the container body for permitting access to the interior of the container body,
   c. barrier means disposed proximate said opening for restricting access to the interior of said container body, at least a portion of said barrier means comprising
  i. a first constriction extending over said opening, and
  ii. a second constriction extending beneath said opening, said second constriction being offset from said first constriction forming an obstruction in the top of said container body, and
d. retention means for preventing items from being dispensed through said opening from the interior of the container body when said container body is upright, at least a portion of said retention means comprising said obstruction.

2. A disposal container according to claim 1 including a closure disposed adjacent said opening.

3. A disposal container according to claim 2 in which said closure is pivotal, and in which said retention means comprises the combination of a portion of said closure shaped to extend across said opening and said obstruction.

4. A disposal container according to claim 3 in which said second constriction comprises a cowl extending into the interior of the container body, said cowl being located at one longitudinal side of said opening and said closure being pivotally disposed at an opposite longitudinal side of said opening.

5. A disposal container according to claim 4 in which said closure pivots about a longitudinal pivot axis, said cowl being radially equidistant from said pivot axis.

6. A disposal container according to claim 3 in which said obstruction extends between said opening and said second constriction, said closure portion having a terminal end shaped to engage said obstruction.

7. A disposal container according to claim 6 including a heel in said closure portion adjacent said terminal end, said heel being shaped to engage said first constriction when said terminal end engages said obstruction.

8. A disposal container according to claim 2 in which said closure is pivotally mounted about a longitudinal pivot axis, said closure comprising a first portion shaped to engage and close said first constriction and a second portion shaped to extend across said opening.

9. A disposal container according to claim 8 including an activation flap extending from and coextensive with a terminal edge of said first portion.

10. A disposal container according to claim 9 in which said closure includes means biasing said closure with said second portion extending across said opening.

11. A disposal container according to claim 10 in which said biasing means comprises a counterweight.

12. A disposal container according to claim 11 in which said counterweight comprises said flap.

13. A disposal container according to claim 2 in which said closure is pivotal, and said first constriction includes means for locking said closure to prevent access to the interior of said container body.

14. A disposal container according to claim 13 in which said first constriction comprises a cowl extending from and above a longitudinal side of said opening, and said locking means comprises at least one catch within said cowl, each said catch including a stop engaging said closure when said closure is pivoted in one direction past said stop into the interior of said cowl, said stop preventing pivoting of said closure in an opposite direction.

15. A disposal container according to claim 1 in which said first constriction comprises a first cowl extending from and above a longitudinal side of said opening and said second constriction comprises a second cowl extending from and beneath said longitudinal side.

16. A disposal system comprising
a. an inner disposal container having a hollow upstanding container body,
b. an opening at the top of the container body for permitting access to the interior of the container body,
c. barrier means disposed proximate said opening for restricting access to the interior of said container body, at least a portion of said barrier means comprising
  i. a first constriction extending over said opening, and
  ii. a second constriction extending beneath said opening,
d. retention means for preventing items from being dispensed through said opening from the interior of the container body when said container body is upright, and
e. a hollow, outer enclosure shaped to accommodate said inner container, said inner container being removable from said outer enclosure.

17. A disposal system according to claim 16 in which said outer enclosure includes a hood, said hood being shaped to conform to said first constriction and being located in registration with said first constriction when said inner container is located within said outer enclosure.

18. A disposal system according to claim 16 including a closure disposed adjacent said opening.

19. A disposal system according to claim 18 in which said closure is pivotal, and in which said retention means comprises the combination of a portion of said closure shaped to extend across said opening and positioning of said second constriction in an offset fashion relative to said opening.

* * * * *